(12) United States Patent
Schubert et al.

(10) Patent No.: US 7,053,116 B2
(45) Date of Patent: May 30, 2006

(54) METHODS FOR PROTECTING CELLS FROM AMYLOID TOXICITY AND FOR INHIBITING AMYLOID PROTEIN PRODUCTION

(75) Inventors: David R. Schubert, La Jolla, CA (US); Yuanbin Liu, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 295 days.

(21) Appl. No.: 10/269,477

(22) Filed: Oct. 11, 2002

(65) Prior Publication Data

US 2003/0096859 A1   May 22, 2003

Related U.S. Application Data

(62) Division of application No. 09/617,147, filed on Jul. 17, 2000, now Pat. No. 6,472,436.

(51) Int. Cl.
*A61K 31/335* (2006.01)
(52) U.S. Cl. .................. 514/452; 514/456; 514/457; 514/866
(58) Field of Classification Search ............ 514/452, 514/456, 457, 866
See application file for complete search history.

(56) References Cited

U.S. PATENT DOCUMENTS

| | | | |
|---|---|---|---|
| 5,783,434 A * | 7/1998 | Tung et al. ............. | 435/219 |
| 5,795,860 A * | 8/1998 | Witt et al. .............. | 514/12 |
| 5,854,204 A | 12/1998 | Findeis et al. | |
| 5,985,242 A | 11/1999 | Findeis et al. | |
| 6,500,846 B1 * | 12/2002 | Hong et al. ............. | 514/321 |

FOREIGN PATENT DOCUMENTS

| | | | |
|---|---|---|---|
| JP | 08268949 | * | 10/1996 |
| WO | WO-97/03661 | * | 2/1997 |

OTHER PUBLICATIONS

Liu et al., "Mechanism of Cellular 3-(4,5-Dimethylthiazol-2-yl)-2,5-Diphenyltetrazolim Bromide (MTT) Reduction",*Journal of Neurochemistry*, vol. 69, No. 2, pp. 581-593 (1997).
Liu et al., "Cytotoxic Amyloid Peptides Inhibit Cellular 3-(4,5-Dimethylthiazol-2-yl)-2,5-Diphenyltetrazolium Bromide (MTT) Reduction by Enhancing MTT Formazan Exocytosis",*Journal of Neurochemistry*, vol. 69, No. 6, pp. 2285-2293 (1997).
Liu et al., "Steroid Hormones Block Amyloid Fibril-Induced 3-(4,5-Dimethylthiazol-2-yl)-2,5-Diphenyltetrazolium Bromide (MTT) Formazan Exocytosis: Relationship to Neurotoxicity", *Journal of Neurochemistry*, vol. 71, No. 6, pp. 2322-2329 (1998).

* cited by examiner

*Primary Examiner*—Kevin E. Weddington
(74) *Attorney, Agent, or Firm*—Foley & Lardner LLP; Stephen E. Reiter

(57) ABSTRACT

In accordance with the present invention, there are provided novel methods of blocking amyloid protein toxicity in cells using polycylic compounds. Also provided are novel methods of decreasing amyloid protein production in cells and methods of inhibiting cell death. Invention methods can be used to prevent and treat a diverse class of disease conditions, known as amyloidoses, which are all related to the occurrence of amyloid protein deposits. Invention methods further provide methods of identifying compounds that can block amyloid toxicity or block the amyloid protein induced inhibition of MMT reduction.

9 Claims, No Drawings

METHODS FOR PROTECTING CELLS FROM AMYLOID TOXICITY AND FOR INHIBITING AMYLOID PROTEIN PRODUCTION

ACKNOWLEDGEMENT

This invention was made with government support under Grant No's. NS09658, NS28121, and 5 F32 NS10279-02 from the National Institutes of Health. The government may have certain rights in the invention.

FIELD OF THE INVENTION

The present invention relates to methods for the treatment and prevention of various amyloidosic disease conditions using one or more of defined classes of polycyclic compounds. In a particular aspect, the invention relates to methods of inhibiting production of amyloid beta peptides, methods of inhibiting aggregation of amyloid fibrils and inhibiting amyloid-induced toxicity.

BACKGROUND OF THE INVENTION

The amyloidoses are a group of pathological conditions in which normally soluble proteins polymerize to form insoluble amyloid fibrils and amyloid deposits. More than 15 proteins form amyloid fibrils resulting in diverse clinical conditions. Amyloidoses are usually classified into systemic amyloidoses and localized amyloidoses. Major systemic amyloidoses include AL amyloidosis, amyloid A amyloidosis, and familial transthyretin amyloidosis; the corresponding amyloid proteins in these amyloidoses are AL amyloid, amyloid A protein, and transthyretin, respectively. Prominent localized amyloidoses include Alzheimer's disease, prion diseases, and type II diabetes; the corresponding amyloid proteins in these diseases are amyloid β peptide, scrapie prion protein, and human amylin, respectively (Sipe (1992) *Annu. Rev. Biochem.* 61:947–975).

Amyloid or amyloid proteins refer to a group of diverse extracellular proteins that form amyloid deposits with common morphological, ultrastructural and physicochemical properties. For example, amyloid deposits have similar affinities for certain dyes and a characteristic appearance under polarized light. Although they vary in amino acid sequence, all amyloid proteins found in amyloid deposits consist of aggregations containing interlacing bundles of parallel arrays of fibrils where the protein in the fibrils is organized in a β-pleated sheet structure.

Amyloidoses share several common features, indeed all are related to amyloid deposits formed by amyloid proteins having different amino acid sequences. For example, many of the amyloid proteins in amyloid deposits are rich in β-pleated sheet conformation, which is responsible for the intensely increased birefingence of amyloid fibrils following Congo red staining (Glenner et al., (1974) *J. Histochem. Cytochem* 22:1141–1158; Glenner and Page (1976) *Int. Rev. Exp. Pathol.* 15:1–92; Glenner (1980) *N. Engl. J. Med.* 302:1283–1292 (Pt. 1) and 133–1343 (Pt. 2)).

Amyloid fibrils, regardless of the amyloid protein from which they are formed, have a cytotoxic effect on various cell types including primary cultured hippocampal neurons (Yankner et al. (1990) *Science* 250:279–282), pancreatic islet β cells (Lorenzo et al. (1994) *Nature* 368:756–760) and clonal cell lines (Behl et al. (1992) *Biochem Biophys. Res. Commun.* 186:944–952; O'Brien et al., (1995) *Am. J. Pathol.* 147:609–616). In fact, only amyloid proteins in fibrillar form are cytotoxic (Pike et al. (1991) *Brain Res.* 563:311–314; Lorenzo and Yankner (1994) *Proc. Natl. Acad. Sci.* 91:12243–12247). It is likely that the cytotoxic effect of fibrils is mediated by a common mechanism (Lorenzo and Yankner (1994) id.; Schubert et al. (1995) *Proc. Natl. Acad. Sci. USA* 92:1989–1993).

Modulation of amyloid protein aggregation is one means of blocking or reducing amyloid toxicity. A detailed description of such modulatory methods can be found in U.S. Pat. No. 5,854,204 (issued Dec. 29, 1998) which is incorporated herein by reference in its entirety.

There is thus a need for additional methods for blocking amyloid protein production and for blocking amyloid toxicity. In particular there is a need for blocking amyloid beta peptide toxicity in neurons, inhibiting the production of amyloid beta peptide, and blocking the production of various other cytotoxic amyloid proteins that result in disease conditions.

SUMMARY OF THE INVENTION

The present invention provides methods of blocking amyloid protein toxicity in cells using one or more of defined classes of polycyclic compounds. Also provided are methods of decreasing amyloid protein production in cells. Invention methods can be used to prevent and treat a diverse class of disease conditions, known as amyloidoses, which are all the result of amyloid protein deposits. In accordance with another embodiment of the invention, there are provided methods of identifying compounds that can block amyloid toxicity or block the amyloid protein induced inhibition of 3-(4,5-dimethylthiazol-2-yl)-2,5-diphenyltetrazolium bromide (MTT) reduction.

DETAILED DESCRIPTION OF THE INVENTION

In accordance with the present invention, there are provided methods of blocking amyloid toxicity in cells, said methods comprising contacting said cells with an effective amount of at least one polycyclic compound selected from biphenyl compounds of Structure I or phenyl benzopyranone compounds of Structure II, wherein said structures are:

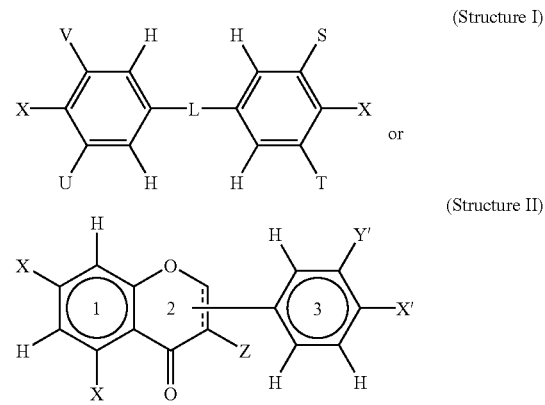

or enantiomers, diasteriomeric isomers or mixtures of any two or more thereof, or pharmaceutically acceptable salts thereof, wherein:

L is $C_1$–$C_{12}$ alkylene, substituted alkylene, cycloalkylene, substituted cycloalkylene or substituted lactone radical;

S, T, U and V are independently OH, halogen, alkyl or substituted alkyl;

each X is independently OH, SH or $NH_2$;

X' is H, SH, $NH_2$ or OR, wherein R is H, lower alkyl, alkenyl, or alkynyl;

Y' is H, OH, SH, or $NH_2$; and

Z is H, OH, SH or $NH_2$;

provided, however, that at least one of Z and Y' is H; or Z is absent when ring 3 is attached at the 3-position of ring 2 of Structure II.

Compounds contemplated for use in the practice of the present invention are those having the structure of Structure I and/or Structure II as set forth herein. In each of these structures, "alkyl" refers to straight or branched chain alkyl radicals having in the range of about 1 up to 12 carbon atoms; "substituted alkyl" refers to alkyl radicals further bearing one or more substituents such as hydroxyl, alkoxy, mercapto, aryl, heterocycle, halogen, trifluoromethyl, pentafluoroethyl, cyano, cyanomethyl, nitro, amino, amide, amidine, amido, carboxyl, carboxamide, carbamate, ester, sulfonyl, sulfonamide, and the like.

As used herein, "$C_1$-$C_{12}$ alkylene" refers to divalent straight or branched chain alkyl moieties having in the range of about 1 up to 12 carbon atoms wherein said moiety serves to link two structures together; "substituted alkylene" refers to alkylene moieties further bearing one or more substituents as set forth above.

As used herein, "cycloalkylene" refers to divalent ring-containing alkyl radicals containing in the range of about 3 up to 20 carbon atoms; "substituted cycloalkylene" refers to cyloalkylene moieties further bearing one or more substituents as set forth above.

As used herein, "halogen" refers to fluoride, chloride, bromide or iodide radicals.

As used herein, "lactone" refers to compounds that are derived by intramolecular elimination of water from a hydroxyl and a carboxyl group of a hydroxyl-substituted carboxylic acid, leading to formation of a cyclic ester; "substituted lactone radical" refers to lactone moieties further bearing one or more substituents as set forth above.

In presently preferred embodiments of the present invention, compounds of Structure I are employed wherein:

L is a substituted lactone radical, alkylene or cycloalkylene;

each X is hydroxyl; and

S, T, U, and V are hydrogen.

In especially preferred embodiments, compounds of Structure I are employed wherein:

L is dimethylmethylene, each X is hydroxyl, and

S, T, U and V are hydrogen, (i.e., bisphenol A) or

L is 1,4-cyclohexylene, each X is hydroxyl, and

S, T, U and V are hydrogen (i.e., 4,4-cyclohexylidenebisphenol) or

L is 2,3-dimethylbutylene, each X is hydroxyl,

U and T are hydroxyl and

S and V are hydrogen (i.e., nordihydroguaiaretic acid) or

L is 5,5-benzofuranonylene;

each X is hydroxyl;

S, T, U and V are hydrogen (i.e. phenolphthalein).

In additional presently preferred embodiments of the present invention, compounds of Structure II are employed, wherein:

each X is hydroxyl,

X' is hydroxyl,

Y' is hydrogen, and

Z is absent as ring 3 is attached at the 3-position of ring 2 (i.e., genistein) or each X is hydroxyl;

X' is hydroxyl,

Y' is hydrogen, and

Z is hydroxyl (i.e., kaempferol) or each X is hydroxyl,

X' is hydroxyl,

Y' is hydrogen, and

Z is hydrogen (i.e., apigenin and naringenin) or each X is hydroxyl,

X' is hydroxyl,

Y' is hydroxyl, and

Z is hydrogen (i.e., luteolin).

Invention methods can optionally be effected using pharmaceutically acceptable salts of the above-described compounds. Such salts are generally prepared by reacting the compounds with a suitable organic or inorganic acid or base. Representative organic salts include methanesulfonate, acetate, oxalate, adipate, alginate, aspartate, valerate, oleate, laurate, borate, benzoate, lactate, phosphate, toluenesulfonate (tosylate), citrate, malate, maleate, fumarate, succinate, tartrate, napsylate, methanesulfonate, 2-naphthalenesulfonate, nicotinate, benzenesulfonate, butyrate, camphorate, camphorsulfonate, cyclopentanepropionate, digluconate, dodecylsulfate, glucoheptanoate, glycerophosphate, heptanoate, hexanoate, undecanoate, 2-hydroxyethanesulfonate, ethanesulfonate, and the like. Representative inorganic salts can be formed from inorganic acids such as sulfate, bisulfate, hemisulfate, hydrochloride, chlorate, perchlorate, hydrobromide, hydroiodide, and the like. Examples of a base salt include ammonium salts; alkali metal salts such as sodium salts, potassium salts, and the like; alkaline earth metal salts such as calcium salts, magnesium salts, and the like; salts with organic bases such as dicyclohexylamine salts, N-methyl-D-glucamine, phenylethylamine, and the like; and salts with amino acids such as arginine, lysine, and the like. Such salts can readily be prepared employing methods well known in the art.

As used herein, the phrase "blocking amyloid toxicity" refers to preventing or inhibiting the harmful and lethal effects on cells and tissues caused by amyloid peptide. While not wishing to be bound by any one mechanism, it is recognized that compositions that prevent or inhibit MTT formazan exocytosis are able to block amyloid toxicity. In addition, compositions that prevent or inhibit the production of amyloid peptide, and compounds that prevent or inhibit the formation of amyloid fibrils are able to block amyloid toxicity.

At excessive levels, amyloid proteins have a cytotoxic effect on cells, resulting in cell death. As used herein, "amyloid toxicity" refers to the deleterious effect of amyloid proteins on cells. Aggregation of amyloid proteins into amyloid fibrils is likely required for its cytotoxic effect, however, the biochemical mechanisms underlying amyloid toxicity are not well understood. Since aggregation appears to be necessary to effect cytotoxicity, inhibiting the aggregation of amyloid proteins into amyloid fibrils and/or inhibiting amyloid fibrils is one means of reducing cytotoxicity.

Amyloid cytotoxicity is related to the rapid inhibition of cellular 3-(4,5-dimethylthiazol-2-yl)-2,5-diphenyltetrazolium bromide (MTT) reduction by amyloid (Behl et al. (1992) *Biochem. Biophys. Res. Commun.* (1994) 186:944–952; Behl et al., (1994) *Cell* 77:817–827; Shearman et al. (1994) *Proc. Natl. Acad. Sci. USA* 91:1470–1474).

MTT is a tetrazolium salt that forms purple-colored, water-insoluble formazan upon reduction (Altman (1976) *Prog. Histochem. Cytochem.* 9:1–56). MTT is taken up by cells through endocytosis and reduced by an N-methylmaleimide-sensitive flavin oxidase. Reduced MTT formazan accumulates in the endosome/lysosome compartment and is then transported to the cell surface through exocytosis (Liu et al. (1997) *J. Neurochem.* 69: 581–593). Because only living cells can reduce MTT, MTT reduction is a widely used method for measuring cell proliferation and viability (Mosmann (1983) *J. Immunol. Methods* 65:55–63). Amyloid proteins such as amyloid beta peptide, human amylin and calcitonin, inhibit cellular MTT reduction by dramatically enhancing MTT formazan exocytosis, thereby suggesting that this phenomenon is closely associated with the cytotoxicity of the amyloid peptides (Liu and Schubert, (1997) *J. Neurochem.* 69:2285–2293).

The ability of an amyloid preparation to induce MTT formazan exocytosis is correlated with its toxicity as measured by exposure of the amyloid preparation to cultured hippocampal neurons and its ability to activate glial cells (see Examples). These two activities have a role in amyloid-induced neurodegeneration.

As used herein, the phrase "contacting" refers to providing compounds to cells or cellular targets. Contacting may take place in solid, liquid or gaseous phase, and refers to events that take place extracellularly and intracellularly. Those of skill in the art will recognize that providing compounds to cells in vivo may be accomplished by numerous modes of administration, including oral, sublingual, intravenous, subcutaneous, transcutaneous, intramuscular, intracutaneous, intrathecal, epidural, intraoccular, intracranial, inhalation, rectal, vaginal, and the like.

As employed herein, the phrase "effective amount", when used in reference to invention methods employing polycyclic compounds, refers to a dose of compound sufficient to provide concentrations high enough to effect the desired result. The specific effective amount for any one compound will depend upon a variety of factors including the type of cell, the severity of the disorder, the activity of the specific compound used, the route of administration, the rate of clearance of the specific compound, the duration of exposure of the cells to the compound, the drugs used in combination or coincident with the specific compound, and the like.

In one embodiment of the present invention, there are provided methods of blocking amyloid toxicity wherein the amyloid toxicity is amyloid beta peptide toxicity. As employed herein, "amyloid beta peptide" (Aβ) refers to proteins of about 40 to 43 amino acid residues. Amyloid beta peptide is predominantly in a 40 amino acid form, i.e., amyloid beta 1-40, however amyloid beta 1-42 and amyloid beta 1-43 are also associated with amyloid fibrils and deposits. The proteins are derived by proteolytic cleavage from their much larger precursor which is known as amyloid beta precursor protein (AβPP). AβPP, a member of a family of amyloid precursor-like proteins, exists in three principal isoforms of 695, 751 and 770 amino acid residues, respectively, each of which contain the amino acid sequence of an amyloid beta peptide. AβPP is synthesized in the rough endoplasmic reticulum, and delivered to the cell surface as an integral membrane protein. AβPP is present in the dendrites, cell bodies and axons of neurons, although its normal neuronal functions are not yet understood. Some of the AβPP in the plasmalemma is internalized into the cell where it is enzymatically processed to an amyloid beta peptide.

AβPP undergoes proteolytic cleavage by several secretases to give rise to various forms of amyloid beta peptide. One type of secretase, γ-secretase, cleaves AβPP in the carboxy-terminal region of the precursor to generate a single copy of an amyloid beta peptide from each precursor molecule. Another type of secretase, α-secretase, cleaves the precursor within the amyloid beta sequence and therefore, cleavage by this secretase does not produce an amyloid beta peptide.

Amyloid beta peptides are the major constituent of the senile plaques found in the central nervous system of patients with Alzheimer's disease. Senile (or neuritic plaques), comprising extracellular deposits of amyloid beta protein, dystrophic axons, and processes of astrocytes and microglia, are distributed throughout the neuropil and in the walls of the cerebral blood vessels.

In accordance with another embodiment of the present invention, there are provided methods of blocking amyloid toxicity wherein the amyloid toxicity is prion protein toxicity. As employed herein, "prion protein" refers to products of the human prion gene (termed PRNP) which is located on the short arm of chromosome 20 and which has an open reading frame consisting of a single exon encoding 254 residues. The normal prion gene product, prion protein (PrP) is a constitutively expressed cell-surface glycoprotein that is bound to the plasmalemma by a glycolipid anchor. The highest levels of PrP messenger RNA are found in neurons of the central nervous system, but the function of the protein is unknown. The normal cellular prion protein and the infectious prion protein do not differ in amino acid sequence, but, similar to amyloid proteins, the normal and infectious proteins have different three-dimensional configurations. Normal prion protein is rich in α-helices, having four putative domains, and little β-pleated sheet configuration. In contrast, the infectious protein has increased β-pleated sheet configuration. The normal and infectious proteins also have different patterns of glycosylation (see *Pathology*, $3^{rd}$ ed. (1999) Rubin and Farber, eds., Lippincott-Raven, pp. 1492–1496).

In accordance with still another embodiment of the present invention, there are provided methods of blocking amyloid toxicity, wherein the amyloid toxicity is amylin toxicity. As used herein, "amylin", which is also known as islet amyloid polypeptide (IAPP) refers to a polypeptide which is secreted along with insulin by the β-cells in the islets of Langerhans. Pancreatic amyloid is found in more than 95% of type II diabetes patients and is formed by the aggregation of islet amyloid polypeptide. Amylin is a 37-residue peptide and various segments within the sequence are sufficient to form β-sheet-containing amyloid fibrils (See e.g., Nilsson and Raleigh *J. Mol. Biol.* 294: 1375–85; Rhoades et al. *Biochim Biophys Acta* (2000) 1476:230–8; and Tenidis et al. *J. Mol. Biol.* (2000) 295: 1055–1071.)

In accordance with yet another embodiment of the present invention, there are provided methods of blocking amyloid toxicity, wherein the amyloid toxicity is amyloid A protein toxicity. As used herein, "amyloid A protein" refers to a polypeptide of about 76 amino acids that is derived from a larger precursor lipoprotein synthesized primarily in the liver, and called serum amyloid A (SAA). Following stimulation of SAA synthesis, SAA is denatured, thereby releasing into the circulation a subunit termed apoSAA, which is internalized by reticuloendothelial cells. Upon release from the reticuloendothelial cells into a fibrillogenic environment containing glycosaminoglycans, serum amyloid P, laminin, collagen IV and Apo E, amyloid fibrils may form, allowing the formation of amyloid deposits (see *Pathology*, $3^{rd}$ ed. supra, pp. 1228–1229).

In accordance with still another embodiment of the present invention, there are provided methods of blocking amyloid toxicity, wherein the amyloid toxicity is transthyretin toxicity. As used herein, "transthyretin" (TTR) refers to a mutated form of a protein that is secreted by the liver into the plasma, where its normal function is to serve as a carrier of thyroid hormones and as a retinal binding protein. At least 60 mutant forms of the protein have been described, each giving rise to a clinical variant of a familial amyloidotic polyneuropathy (FAP). The most common variant of FAP is due to transthyretin, where there is an amino acid substitution at residue 30 of methionine for valine. The sequence modification lowers the stability of the tetrameric TTR, allowing the formation of a monomeric intermediate with an altered conformation (see *Pathology*, $3^{rd}$ ed. supra, pp. 1225, 1228).

In accordance with yet another embodiment of the present invention, there are provided methods of blocking amyloid toxicity, wherein the amyloid toxicity is AL amyloid toxicity. As used herein, "AL amyloid" refers to a protein that consists of the variable region of immunoglbulin light chains and can be derived from either the kappa (κ) or lambda (λ) moieties. Excess production of immunoglobulins results in their secretion into the circulatory system which provides a fibrillogenic environment due to the presence of glycosaminoglycans, serum amyloid P, laminin, collagen IV and ApoE. Amyloid fibrils that form are then processed proteolytically in various types of cells, including macrophages, Kupffer cells and endothelial cells, resulting in the formation of amyloid deposits (see *Pathology*, $3^{rd}$ ed. supra, pp. 1226–1227).

In accordance with still another embodiment of the present invention, there are provided methods for decreasing amyloid protein production in cells, said method comprising contacting said cells with an effective amount of at least one compound of Structure I and/or Structure II, as described above, or enantiomers, diasteriomeric isomers or mixtures of any two or more thereof, or pharmaceutically acceptable salts thereof.

Decreasing amyloid protein production can block or prevent the cytotoxic effects on cells of excessive levels of amyloid protein, and block or prevent the formation of amyloid plaques, such as those associated with various amyloid-related diseases. Various means of decreasing amyloid protein production are contemplated including reducing or preventing the production of an amyloid precursor protein, reducing or preventing the proteolytic cleavage that generates amyloid protein, reducing or preventing post-translational modification of amyloid protein, reducing or preventing internalization of amyloid precursor protein by increasing membrane stabilization, and the like.

In preferred embodiments of the invention, amyloid protein production is blocked or prevented by decreasing amyloid beta peptide, amyloid prion protein, islet amyloid protein (amylin), amyloid A protein, transthyretin or AL amyloid.

In accordance with yet another embodiment of the invention, there are provided methods of inhibiting nerve cell death, said methods comprising contacting the nerve cells with an effective amount of at least one compound of Structure I and/or of Structure II.

As used herein, "nerve cell death" refers to a reduction in nerve cell number or to a loss of nerve cell function. Nerve cell death can occur through activation or acceleration of an apoptotic pathway, i.e., programmed cell death, or through a necrotic cell death which does not involve activation of an endogenous cell death program. Necrotic cell deaths often result from acute traumatic injury and typically involve rapid lysis of cellular membranes. Inhibiting nerve cell death can reduce the loss of nerve cells or the loss of nerve cell function that is associated with both types of nerve cell death.

In accordance with still another embodiment of the present invention, methods are provided for treating a disease condition in a subject in need thereof, said method comprising administering to the subject a therapeutically effective amount of a compound of Structure I and/or Structure II.

As used herein, "treating" refers to inhibiting or arresting the development of a disease, disorder or condition and/or causing the reduction, remission, or regression of a disease, disorder or condition. Those of skill in the art will understand that various methodologies and assays may be used to assess the development of a disease, disorder or condition, and similarly, various methodologies and assays may be used to assess the reduction, remission or regression of a disease, disorder or condition.

Essentially, any disease that is etiologically linked to the formation and/or deposition of amyloid is contemplated for treatment according to the present invention. As used herein, "disease condition" refers to a disorder such as Alzheimer's disease, systemic senile amyloidosis, prion disease, scrapie, bovine spongiform encephalopathy, Creutzfeldt-Jakob disease, Gerstmann-Straussler-Scheinker syndrome, type II diabetes, adult onset diabetes, insulinoma, amyloid A amyloidosis, AL amyloidosis, familial amyloid polyneuropathy (Portuguese, Japanese and Swedish types), familial transthyretin amyloidosis, familial Mediterranean Fever, familial amyloid nephropathy with urticaria and deafness (Muckle-Wells syndrome), hereditary non-neuropathic systemic amyloidosis (familial amyloid polyneuropathy III), familial amyloidosis of Finnish type, familial amyloid cardiomyopathy (Danish type), isolated cardiac amyloid, isolated atrial amyloidosis, idiopathic (primary) amyloidosis, myeloma or macroglobulinemia-associated amyloidosis, primary localized cutaneous nodular amyloidosis associated with Sjogren's syndrome, reactive (secondary) amyloidosis, hereditary cerebral hemorrhage with amyloidosis of Icelandic type, amyloidosis associated with long term hemodialysis, fibrinogen-associated hereditary renal amyloidosis, amyloidosis associated with medullary carcinoma of the thyroid, lysozyme-associated hereditary systemic amyloidosis, and the like.

Amyloid deposits are found in subjects diagnosed with Alzheimer's disease, a neurodegenerative disease characterized by atrophy of nerve cells in the cerebral cortex, sub-cortical areas, and hippocampus and the presence of plaques, dystrophic neurites and neurofibrillary tangles. In Alzheimer's disease, dystrophic or aberrant neurite growth, synapse loss, and neurofibrillary tangle formation are strong correlates of disease severity. Dystrophic neurons characteristically contain abundant electrodense multilaminar bodies in the cytoplasm of the neurites and have disruption of synaptic junctions. The dystrophic neurons surround deposits of amyloid, thereby forming the senile plaques located throughout the brain neuropil as well as in the walls of cerebral blood vessels. Invention methods for treating Alzheimer's disease can reduce or block the atrophy of nerve cells, reduce or block the formation of senile plaques or neurofibrillary tangles, and the like, such that the development of the disease is slowed or arrested.

Amyloid deposits are also found in the islets of Langerhans in patients diagnosed with type II diabetes. The deposits contain an amyloid protein that is derived from a larger precursor called islet amyloid polypeptide (IAPP) or amylin which, in normal animals, has a hormonal role. IAPP is produced by the β-cells of the islets and has a profound effect on glucose uptake by the liver and striated muscle cells. In transgenic mice having a transgene for human amylin and which are fed a high fat diet, overproduction of amylin leads to islet amyloid deposition (see *Pathology*, 3$^{rd}$ ed. (1999) supra, p. 1226). Invention methods for treating amyloid deposits in the islets of Langerhans in patients having type II diabetes can reduce or prevent the formation of amyloid protein, reduce or prevent the deposition of amyloid protein into amyloid deposits, and the like.

Yet another disease where amyloid deposits are noted is prion disease, one type of spongiform encephalopathy. Prion diseases are neurodegenerative conditions characterized clinically by progressive ataxia and dementia, and pathologically by vacuolization of spongiform brain tissue. Amyloid deposits are associated with at least one prion disease known as kuru. In kuru, about 70% of prion protein accumulates extracellulary to form plaques, in contrast to normal prion protein which is a constitutively expressed cell-surface glycoprotein (see *Pathology*, 3$^{rd}$ ed. supra, pp. 1492–1496). Invention methods for treating prion disease can reduce or prevent the production of amyloid protein, reduce or prevent the deposition of amyloid plaques, and the like.

Still another disease where amyloid deposits are noted is amyloid A amyloidosis. Amyloid A amyloidoses refer to amyloidoses from seemingly unrelated disorders such as chronic inflammatory disorders, neoplastic disorders, and hereditary disorders. The deposition of amyloid protein is secondary to the underlying disease condition. The precursor molecule is serum amyloid A (SAA), an acute phase reactant, which can be used as a surrogate marker of inflammation in many diseases. Invention methods for treating amyloid A amyloidosis can reduce or prevent the production of amyloid protein, reduce or prevent the production of the precursor to amyloid protein, prevent or reduce any one of several steps necessary to generate an active amyloid protein, reduce or prevent the deposition of amyloid plaques, and the like.

Yet another disease where amyloid deposits are noted is familial transthyretin amyloidosis which is the most common form of Familial Amyloidotic Polyneuropathy (FAP). The human amyloid disorders, familial amyloid polyneuropathy, familial amyloid cardiomyopathy and senile systemic amyloidosis, are caused by insoluble transthyretin (TTR) fibrils, which deposit in the peripheral nerves and heart tissue. Transthyretin is a homotetrameric plasma protein implicated in the transport of thyroxine and retinol. The most common amyloidogenic TTR variant is V30M-TTR, while L55P-TTR is the variant associated with the most aggressive form of FAP. Invention methods for treating amyloidoses caused by transthyretin can reduce or prevent the production of amyloid protein, reduce or prevent the production of the precursor to amyloid protein, prevent or reduce any one of several steps necessary to generate an active amyloid protein, reduce or prevent the deposition of amyloid plaques, and the like.

A further disease where amyloid deposits are noted is AL amyloidosis. AL amyloidosis is a class of diseases related to a primary disorder of immunoglobulin production which includes primary amyloidosis, plasma cell dyscrasia, immunoblastic lymphoma, multiple myeloma, and the like. Primary systemic AL (amyloid light-chain) amyloidosis is a plasma cell disorder in which depositions of amyloid light-chain protein cause progressive organ failure. The prognosis of primary amyloidosis is generally poor, with a median survival of 1–2 years. The precursor protein is an immunoglobulin light chain in both localized and systemic AL-amyloidosis which shows the same pattern of fragmentation and changes of primary structure. Invention methods for treating amyloidoses caused by AL amyloid proteins can reduce or prevent the production of amyloid protein, reduce or prevent the production of the precursor to amyloid protein, prevent or reduce any one of several steps necessary to generate an active amyloid protein, reduce or prevent the deposition of amyloid plaques, and the like.

As used herein, "administering" refers to providing a therapeutically effective amount of a compound to a subject, using oral, sublingual, intravenous, subcutaneous, transcutaneous, intramuscular, intracutaneous, intrathecal, epidural, intraoccular, intracranial, inhalation, rectal, vaginal, and the like administration. Administration in the form of creams, lotions, tablets, capsules, pellets, dispersible powders, granules, suppositories, syrups, elixirs, lozenges, injectable solutions, sterile aqueous or non-aqueous solutions, suspensions or emulsions, patches, and the like, is also contemplated. The active ingredients may be compounded with non-toxic, pharmaceutically acceptable carriers including, glucose, lactose, gum acacia, gelatin, mannitol, starch paste, magnesium trisilicate, talc, corn starch, keratin, colloidal silica, potato starch, urea, dextrans, and the like.

The preferred route of administration will vary with the clinical indication. Some variation in dosage will necessarily occur depending upon the condition of the patient being treated, and the physician will, in any event, determine the appropriate dose for the individual patient. The effective amount of compound per unit dose depends, among other things, on the body weight, physiology, and chosen inoculation regimen. A unit dose of compound refers to the weight of compound employed per administration event without the weight of carrier (when carrier is used).

Targeted-delivery systems, such as polymer matrices, liposomes, and microspheres can increase the effective concentration of a therapeutic agent at the site where the therapeutic agent is needed and decrease undesired effects of the therapeutic agent. With more efficient delivery of a therapeutic agent, systemic concentrations of the agent are reduced because lesser amounts of the therapeutic agent can be administered while accruing the same or better therapeutic results. Methodologies applicable to increased delivery efficiency of therapeutic agents typically focus on attaching a targeting moiety to the therapeutic agent or to a carrier which is subsequently loaded with a therapeutic agent.

Various drug delivery systems have been designed by using carriers such as proteins, peptides, polysaccharides, synthetic polymers, colloidal particles (i.e., liposomes, vesicles or micelles), microemulsions, microspheres and nanoparticles. These carriers, which contain entrapped pharmaceutically useful agents, are intended to achieve controlled cell-specific or tissue-specific drug release.

The compounds described herein can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The compounds described herein, when in liposome form can contain, in addition to the compounds described herein, stabilizers, preservatives, excipients, and the like. The preferred lipids are the phospholipids and the phosphatidyl cholines (lecithins), both natural and synthetic. Methods to form liposomes are known in the art. (See, e.g., Prescott, Ed., Methods in Cell Biology, Volume XIV, Academic Press, New York, N.Y., (1976), p 33 et seq.)

Several delivery approaches can be used to deliver therapeutic agents to the brain by circumventing the blood-brain barrier. Such approaches utilize intrathecal injections, surgical implants (Ommaya, *Cancer Drug Delivery*, 1:169–178 (1984) and U.S. Pat. No. 5,222,982), interstitial infusion (Bobo et al., *Proc. Natl. Acad. Sci. U.S.A.*, 91:2076–2080 (1994)), and the like. These strategies deliver an agent to the CNS by direct administration into the cerebrospinal fluid (CSF) or into the brain parenchyma (ECF).

Drug delivery to the central nervous system through the cerebrospinal fluid is achieved, for example, by means of a subdurally implantable device named after its inventor the "Ommaya reservoir". The drug is injected into the device and subsequently released into the cerebrospinal fluid surrounding the brain. It can be directed toward specific areas of exposed brain tissue which then adsorb the drug. This adsorption is limited since the drug does not travel freely. A modified device, whereby the reservoir is implanted in the abdominal cavity and the injected drug is transported by cerebrospinal fluid (taken from and returned to the spine) to the ventricular space of the brain, is used for agent administration. Through omega-3 derivatization, site-specific biomolecular complexes can overcome the limited adsorption and movement of therapeutic agents through brain tissue.

Another strategy to improve agent delivery to the CNS is by increasing the agent absorption (adsorption and transport) through the blood-brain barrier and the uptake of therapeutic agent by the cells (Broadwell, *Acta Neuropathol.*, 79: 117–128 (1989); Pardridge et al., *J. Pharmacol. Experim. Therapeutics*, 255: 893–899 (1990); Banks et al., *Progress in Brain Research*, 91:139–148 (1992); Pardridge, *Fuel Homeostasis and the Nervous System*, ed.: Vranic et al., Plenum Press, New York, 43–53 (1991)). The passage of agents through the blood-brain barrier to the brain can be enhanced by improving either the permeability of the agent itself or by altering the characteristics of the blood-brain barrier. Thus, the passage of the agent can be facilitated by increasing its lipid solubility through chemical modification, and/or by its coupling to a cationic carrier, or by its covalent coupling to a peptide vector capable of transporting the agent through the blood-brain barrier. Peptide transport vectors are also known as blood-brain barrier permeabilizer compounds (U.S. Pat. No. 5,268,164). Site specific macromolecules with lipophilic characteristics useful for delivery to the brain are described in U.S. Pat. No. 6,005,004.

Other examples (U.S. Pat. No. 4,701,521, and U.S. Pat. No. 4,847,240) describe a method of covalently bonding an agent to a cationic macromolecular carrier which enters into the cells at relatively higher rates. These patents teach enhancement in cellular uptake of bio-molecules into the cells when covalently bonded to cationic resins.

U.S. Pat. No. 4,046,722 discloses anti-cancer drugs covalently bonded to cationic polymers for the purpose of directing them to cells bearing specific antigens. The polymeric carriers have molecular weights of about 5,000 to 500,000. Such polymeric carriers can be employed to deliver compounds described herein in a targeted manner.

Further work involving covalent bonding of an agent to a cationic polymer through an acid-sensitive intermediate (also known as a spacer) molecule, is described in U.S. Pat. No. 4,631,190 and U.S. Pat. No. 5,144,011. Various spacer molecules, such as cis-aconitic acid, are covalently linked to the agent and to the polymeric carrier. They control the release of the agent from the macromolecular carrier when subjected to a mild increase in acidity, such as probably occurs within a lysosome of the cell. The drug can be selectively hydrolyzed from the molecular conjugate and released in the cell in its unmodified and active form. Molecular conjugates are transported to lysosomes, where they are metabolized under the action of lysosomal enzymes at a substantially more acidic pH than other compartments or fluids within a cell or body. The pH of a lysosome is shown to be about 4.8, while during the initial stage of the conjugate digestion, the pH is possibly as low as 3.8.

As employed herein, the phrase "therapeutically effective amount", when used in reference to invention methods employing polycyclic compounds, refers to a dose of compound sufficient to provide circulating concentrations high enough to impart a beneficial effect on the recipient thereof. The specific therapeutically effective dose level for any particular patient will depend upon a variety of factors including the disorder being treated, the severity of the disorder, the activity of the specific compound used, the route of administration, the rate of clearance of the specific compound, the duration of treatment, the drugs used in combination or coincident with the specific compound, the age, body weight, sex, diet and general health of the patient, and like factors well known in the medical arts and sciences. Dosage levels typically fall in the range of about 0.001 up to 100 mg/kg/day; with levels in the range of about 0.05 up to 10 mg/kg/day being preferred.

In accordance with still another embodiment of the invention, there are provided methods for preventing disease conditions in a subject at risk thereof, said methods comprising administering to said subject a therapeutically effective amount of at least one of the compounds described herein.

As used herein, the phrase "preventing disease conditions" refers to averting a disease, disorder or condition from occurring in a subject who may be at risk for the disease, but has not yet been diagnosed as having the disease. Those of skill in the art will understand that a variety of methods may be used to determine a subject at risk for a disease, and that whether a subject is at risk for a disease will depend on a variety of factors known to those of skill in the art, including genetic make-up of the subject, age, body weight, sex, diet, general health, occupation, exposure to environmental conditions, marital status, and the like, of the subject.

In accordance with a further embodiment of the present invention, there are also provided methods of identifying compound(s) that reduce(s) or prevent(s) amyloid toxicity, said methods comprising (a) incubating the compound with MTT, an amyloid protein, and a cell; and (b) comparing the amount of MTT formazan at the cell surface of the cell incubated with the compound with the amount of MTT formazan at the cell surface of a cell not incubated with the compound, wherein a decrease in the amount of MTT formazan at the cell surface is indicative of a decrease in cytotoxic amyloid protein-induced inhibition of MTT reduction, thereby allowing identification of a compound that reduces or prevents amyloid toxicity.

As used herein, "incubating" refers to conditions which allow contact between the test compound and the cell of interest. The cell may be any cell of interest including neuronal cells, glial cells, cardiac cells, bronchial cells, uterine cells, testicular cells, liver cells, renal cells, intestinal cells, cells from the thymus and spleen, placental cells, endothelial cells, endocrine cells including thyroid, parathyroid, pituitary, and the like, smooth muscle cells, skeletal muscle cells, and the like.

Compounds that block amyloid toxicity include peptides, peptidomimetics, polypeptides, pharmaceuticals, biological agents, and the like. Antibodies, tropic agents, and combinatorial compound libraries can also be tested using the invention method. One class of preferred compounds are organic molecules, more preferably small organic compounds having a molecular weight of more than about 50 and less than about 2,500 Daltons. The test compound may also be provided as part of a combinatorial library to allow screening of a plurality of compounds.

Candidate compounds can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate agents are also found among biomolecules including peptides, saccharides, fatty acids, steroids, purines, pyrimidines, derivatives, structural analogs or combinations thereof, and the like.

A variety of other agents may be included in the screening assay. These include agents like salts, natural proteins, e.g., albumin, detergents, etc. that are used to facilitate optimal protein-protein binding and/or reduce nonspecific or background interactions. Reagents that improve the efficiency of the assay, such as protease inhibitors, nuclease inhibitors, antimicrobial agents, and the like may be used. The mixture of components can be added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 10 h will be sufficient.

In accordance with yet another embodiment of the present invention, there are provided methods of identifying a compound that reduces or prevents amyloid protein induced inhibition of MTT reduction, said methods comprising (a) incubating the compound with MTT, a cytotoxic amyloid protein, and a cell that is reducing MTT; and (b) comparing the amount of MTT formazan at the cell surface of the cell incubated with the compound with the amount of MTT formazan at the cell surface of a cell not incubated with the compound, wherein a decrease in the amount of MTT formazan at the cell surface is indicative of a decrease in cytotoxic amyloid protein-induced inhibition of MTT reduction, thereby allowing the identification of a compound that reduces or prevents cytotoxic amyloid protein induced inhibition of MTT reduction.

In accordance with still another embodiment of the present invention, there are provided methods of modulating the aggregation of amyloid proteins. Modulation of amyloid protein aggregation can prevent or delay the onset of a disease associated with amyloid deposition. In a method of modulating aggregation of amyloid proteins, amyloid proteins are contacted with compounds described herein such that the aggregation of amyloid proteins is altered. As used herein, the term "modulating" refers to both inhibition of amyloid aggregation and promotion of amyloid aggregation. Aggregation of amyloid proteins is inhibited by one or more compounds described herein when there is a decrease in the amount and/or rate of amyloid aggregation in the presence of one or more compounds described herein as compared to the amount and/or rate of amyloid aggregation in the absence of the same one or more compounds. Inhibition of aggregation includes both complete and partial inhibition of aggregation of amyloid proteins. Inhibition of aggregation can be quantitated as the fold increase in the lag time for aggregation or as the decrease in the overall plateau level of aggregation (i.e., total amount of aggregation), using an aggregation assay known to those of skill in the art. Alternatively, aggregation of amyloid proteins is promoted by one or more compounds described herein when there is an increase in the amount and/or rate of amyloid aggregation in the presence of one more or more compounds described herein compared to the amount and/or rate of amyloid aggregation in the absence of one or more of the same compounds.

The following examples are intended to illustrate but not to limit the invention in any manner, shape, or form, either explicitly or implicitly. While they are typical of those that might be used, other procedures, methodologies, or techniques known to those skilled in the art may alternatively be used.

EXAMPLE 1

Materials and cell lines All amyloid peptides are obtained from Bachem California. The peptides are dissolved either in dimethyl sulfoxide ($A\beta_{1-42}$ and $A\beta_{1-40}$) or in water (all other peptides) at 0.5 mM (human amylin) or 1 mM (all other amyloid peptides) concentration, aliquoted, and stored at −20° C. before use. The dishes are then rotated ten times to make a homogenous dilution. All other reagents are from Sigma or Calbiochem.

B12 cells are from a collection of cells made from nitrosoethyl-urea-induced rat brain tumors (Schubert et al. (1974) *Nature* 249:224–227). These cells respond to $A\beta$ with some initial cell lysis (20–30%; Behl et al. (1994) *Cell* 77:817–927) and a decreased ability to reduce MTT. Primary cultures of rat cortical neurons are prepared as described elsewhere (Behl et al. (1994) supra). The rat pheochromocytoma PC12 cells are a subclone of cells originally obtained from L. Greene (Green and Tischler (1976) *Proc. Natl. Acad. Sc. USA* 73:2424–2428).

MTT reduction and MTT formazan exocytosis MTT reduction by cultured cells was performed in 96-well microtiter plates containing 100 µl of medium per well. Cells (about $10^4$ cells per well) were plated in Dulbecco's modified Eagles's medium (DMEM) supplemented with 5% dialyzed fetal calf serum and incubated overnight before drug treatment. MTT reduction was started by adding 10 µl per well of a 2.5 mg/ml MTT stock in phosphate-buffered saline (PBS) and terminated by adding 100 µl of a solubilization solution containing 50% N,N'-dimethylformamide and 20% sodium dodecyl sulfate (SDS; pH 4.8). To test the ability of a compound to reduce or prevent amyloid induced inhibition of MTT reduction on cultured cells, the stock solution of the amyloid peptides is added directly to culture dishes containing cultured cells. Following the addition of amyloid proteins, test compounds are added at concentrations appropriate to effect a change in MTT reduction and/or MTT formazan exocytosis. MTT reduction is determined the next day by determining absorbance at 570 nm with an automatic microtiter plate reader, using 630 nm as the reference wavelength.

MTT formazan exocytosis is assessed by microscopic observation. The needle-like crystals on the surface of the cells incubated with MTT, which are easily visible under a light microscope, represent exocytosed MTT formazan (Liu et al. (1997) *J. Neurochem.* 69:581–593). The percentages of cells exocytosing MTT formazan were determined by counting 300 cells in multiple fields using the presence of needle-like formazan crystals on cell surface as an indicator of MTT formazan exocytosis. A cell is counted as exocytosing MTT formazan when several needle-like formazan crystals are clearly visible.

Photomicroscopy. Cells growing on 35-mm dishes were examined and photographed with a Nikon light microscope equipped with a water immersible object lens using Kodak EPT 56T film.

EXAMPLE 2

Inducing Cellular MTT Formazan Exocytosis is a Property of Protein Fibrils With a Cross-β Structure MTT reduction by living cells is initially observed as intracellular formazan granules, and needle-like formazan crystals begin to appear on the cell surface after about 30 min of MTT reduction. These intracellular MTT formazan-containing granules are acidic endosomes/lysosomes and the needle-like MTT formazan crystals on the cell surface result from the exocytosis of the intracellular MTT-containing vesicles (Liu et al., *J. Neurochem.* 69:581–593 (1997)). B12 cells, a rat neural cell line (Schubert, supra (1974)), begin to exocytose MTT formazan after 30 min of MTT reduction (2 to 5% of the cells are positive), and it takes more than 3 hours for over 90% of the cells to exhibit exocytosed MTT formazan. Amyloid peptides ($A\beta_{25-35}$, $A\beta_{1-40}$, $A\beta_{1-42}$, human amylin) that can form fibrils with a cross-β-pleated sheet structure dramatically enhance MTT formazan exocytosis. After only 30 min of MTT reduction in the presence of amyloid peptide, more than 95% of the cells exhibit exocytosed MTT formazan. Nonfibrillogenic peptides (such as $A\beta_{1-28}$, $A\beta_{17-40}$, $A\beta_{40-1}$, scrambled $A\beta_{25-35}$ and rat amylin) do not enhance MTT formazan exocytosis (Liu and Schubert *J. Neurochem.* 69:2285–2293 (1997)).

The formazan crystals induced by fibrillogenic amyloid peptides appear different from the formazan crystal of cells not exposed to amyloid peptides. Amyloid-induced formazan crystals are shorter, thicker and more violet in color. Because amyloid peptide-induced MTT formazan exocytosis can be visually distinguished from that occurring naturally, detection of Aβ-induced MTT formazan exocytosis at concentrations as low as 25 nM $A\beta_{1-42}$ is possible.

The involvement of β-sheeted amyloid fibrils in generating this phenomenon is supported by the observation that amyloid-binding agents such as Congo red block 90% of the Aβ-induced MTT formazan exocytosis. Under denaturing conditions, non-amyloidogenic proteins such as insulin and glucagon also form protein fibrils with the same cross β structure as that in amyloid fibrils (Glenner et al., *J. Histochem. Cytochem.* 22:1141–1158 (1974) and Burke et al. *Biochem.* 11:2435–2439 (1972)). These protein fibrils also induce MTT formazan exocytosis that is indistinguishable from that caused by Aβ (Liu and Schubert *J. Neurochem.* 71:2322–2329 (1998)). Therefore, the ability to enhance cellular MTT formazan exocytosis is a common property of protein fibrils having a cross β-pleated sheet structure. Although the active amyloid species that induce this phenomenon is most likely to be the cross β-sheeted amyloid fibrils, it is possible that some β-sheet-containing prefibrillar intermediates (such as protofibrils, see Lansbury, *Proc. Natl. Acad. Sci. USA* 96:3342–3343 (1999)) can also contribute.

EXAMPLE 3

Methods of Identifying Compounds that Reduce or Prevent Amyloid Toxicity

Compounds that block amyloid-dependent toxicity can be assessed using the assays described herein.

The results obtained when compounds described herein are subjected to assays described herein are summarized in Tables 1 and 2.

TABLE 1

Activity of Compounds of Structure I

| NO | L | S | T | U | V | X* | ACTIVITY |
|---|---|---|---|---|---|---|---|
| Compounds Useful in Invention Methods | | | | | | | |
| 1 | dimethylmethylene | H | H | H | H | OH, OH | + |
| 2 | 1,4-cyclohexylene | H | H | H | H | OH, OH | + |
| 3 | 2,3-dimethylbutylene | H | OH | OH | H | OH, OH | + |
| 4 | 5,5-benzofuranonylene | H | H | H | H | OH, OH | + |
| Comparison Compounds | | | | | | | |
| 5 | none | H | H | H | H | OH, OH | − |
| 6 | dimethylmethylene | OH | H | H | H | OH, H | − |
| 7 | 3,4-hexylene | H | H | H | H | OH, OH | − |
| 8 | dimethylmethylene | H | H | H | H | H, OH | − |
| 9 | dimethylmethylene | H | H | H | H | H, H | − |
| 10 | dimethylmethylene | H | H | H | H | —O(CH$_2$)$_2$O(CH$_2$)$_2$OH, —O(CH$_2$)$_2$O(CH$_2$)$_2$OH | − |

*Substituents are at the 4 and 4' positions, respectively.

TABLE 2

Activity of Compounds of Structure II

| NO. | X** | X' | Y' | Z | Ring position* | Activity |
|---|---|---|---|---|---|---|
| Compounds Useful in Invention Methods | | | | | | |
| 1 | OH, OH | OH | H | NP | 3 | + |
| 2 | OH, OH | OH | H | H | 2 | + |
| 3 | OH, OH | OH | H | H | 2 | + |
| 4 | OH, OH | OH | OH | H | 2 | + |
| 5 | OH, OH | OH | H | OH | 2 | + |

TABLE 2-continued

Activity of Compounds of Structure II

| NO. | X** | X' | Y' | Z | Ring position* | Activity |
|---|---|---|---|---|---|---|
| 6 | OH, H | OCH$_3$ | OH | H | 2 | +− |
| 7 | OH, OH | H | H | H | 2 | +− |
| Comparison Compounds | | | | | | |
| 8 | H, OH | OH | H | NP | 3 | − |
| 9 | OH, OH | OH | OH | OH | 2 | − |

*Ring Position refers to the point of attachment of ring 3 to ring 2. When ring 3 is attached at the 3-position, Z is absent.
**Substituents are at the ortho and meta positions, repsectively.
+− indicates variable results in activity assays, or results near threshold.

Inspection of the data presented in Tables 1 and 2 reveal that several compounds described herein display activity in an in vitro assay.

EXAMPLE 4

Neurotoxicity and glial activation are two biological activities of amyloid which are critical components of pathways leading to neurodegeneration. To study whether amyloid peptide-induced MTT formazan exocytosis is an indicator or marker of bioactive amyloid fibrils, the correlation between amyloid fibril-induced MTT formazan exocytosis and these two biological activities of amyloid was investigated.

Hippocampal neuronal cultures and assessment of neuronal viability Hippocampal neurons were prepared from 18-day-old embryos of Sprague-Dawley rats and enzymatically dissociated as described before (Liu and Schubert (1998) *J. Neurochem.* 71:2322–2399, Liu and Schubert (1997) *J. Neurochem.* 69:2285–2293). The cells were suspended in a serum-free medium and plated on polylysine-coated 24-well tissue culture plates ($1 \times 10^6$ cells/ml). The serum-free medium used is a modified minimal essential medium containing 30 mM glucose, 2 mM glutamine, 1 mM pyruvate, penicillin (100 U/ml), streptomycin (100 µg/ml), and N1supplements (Sigma). After 3 days in culture, the neurons acquire long and extensively branched neurites. Half of the medium in each dish was then replaced with fresh medium, and test reagents (20 µM peptide solutions) were added. Neuron survival was assessed 48 hours after treatment. Neurons were judged to be viable by the intactness of their neurites and soma (absence of vacuoles and the ability to exclude trypan blue). Five fields (~80 neurons/field) were scored in each culture. The number of viable neurons in untreated cultures was designated as 100% survival.

Astrocyte culture and quantitation of secreted cytokines Primary astrocytes were prepared from the cortices of 2-day-old Sprague-Dawley rat pups according the method of Levison and McCarthy (*Culturing Nerve Cells* in: G. Banker, and K. Goslin (eds.), MIT Press, Cambridge, Mass. 1991, pp. 309–336). The dissected cortices were dissociated enzymatically with trypsin and mechanically by passing through a fine pipette. The cells were cultured in α-MEM (Life Technologies, MD) containing 10% fetal bovine serum and antibiotics. After 11 days in culture, the primary cells were replated at a density of 10,000 cells/cm$^2$ and grown until confluent. At least 24 hr before treatment, the cells were washed twice with PBS and then incubated with serum-free α-MEM containing N$_2$ supplements (Life Technologies, MD).

Cytokine Measurements For IL-1β and TNF-α measurements, $7.5 \times 10^4$ cells/well were plated in a 48-well tissue culture plate. After 48 hr of incubation in serum-free α-MEM containing N$_2$ supplements, the cells were treated with 10 µM of various amyloid or non-amyloidogenic peptides for 12 hr. Conditioned media from duplicate wells for each sample were collected and stored at −80° C. until use. Cytokine levels in the conditioned media were determined by ELISA kits from R&D systems and performed according to the manufacturer's protocols.

Electron microscopy To determine the presence or absence of fibrils in peptide preparations, a 5 µl sample of 0.25 mM amyloid peptide suspension was placed on a Formvar-carbon-coated 200-mesh copper grid for 5 min. The sample was negatively stained with 1% phosphotungistic acids (w/v, pH 7.0) and air dried after absorbing excess liquid on the grid with filter paper. Specimens were examined in a JEM-100 CX II electron microscope operated at an accelerating voltage of 80 kV.

Congo red birefringence Congo red birefringence of amyloid preparations was demonstrated using the following protocol. A 10 µl sample of a 0.25 mM amyloid peptide suspension was mixed with 10 µl 1% aqueous Congo red (pH 10) and then placed on a glass slide. Birefringence was observed with a Nikon light microscope equipped with polarization filters.

EXAMPLE 5

The Ability of Amyloid Peptides to Induce Neurotoxicity and to Activate Glia is Closely Correlated With Their Ability to Induce MTT Formazan Exocytosis Aβ neurotoxicity is readily demonstrated in primary cultured hippocampal neurons (Yankner et al., *Science* 250: 279–282 (1990) and as described herein), and glial activation is evidenced either by the morphological change of the astrocytes into an active phenotype (Pike et al., *Neuroscience* 63:517–531 (1994) and Hu et al., *Brain Res.* 785195–206 1998)) or by increased cytokine secretion of the glial cell (Meda, *Nature* 374:647–650 (1995); Yates et al., *J. Neurochem.*, 74:1017–1025 (2000); Akama and Van Eldik, *J. Biol. Chem.* 275:7918–7924 (2000); and as described herein).

Aβ$_{25-35}$ and Aβ$_{1-42}$ are always active in inducing MTT formazan exocytosis when solubilized in deionized water. The ability of Aβ$_{1-40}$ preparations to induce MTT formazan exocytosis is variable among different manufacturer's lots. Lots of active and inactive Aβ$_{1-40}$ preparations were used to illustrate the relationship among amyloid fibril formation, MTT formazan exocytosis, neurotoxicity and astrocyte activation. The presence of amyloid fibrils in a peptide preparation (as revealed by electron microscopy and Congo red birefringence) is directly correlated with the abilities of a peptide preparation to affect MTT formazan exocytosis, to induce neurotoxicity and to activate astrocytes.

Peptide preparations that contain β-sheeted amyloid fibrils (Aβ$_{1-40}$/lot QQL448 and human amylin) induce MTT formazan exocytosis, kill rat hippocampal neurons and activate astrocytes as indicated by the morphological changes of the astrocytes. In contrast, peptide preparations which do not contain amyloid fibrils (Aβ$_{1-40}$ lot WM226 and rat amylin) are not active in any of the three assays. These results suggest a tight link between amyloid fibril formation and biological activities of a peptide preparation, and also suggest that the three observed biological activities of an amyloid peptide are closely associated. Similar data are obtained with additional lots of active or inactive $A\beta_{1-40}$ and other amyloid or nonamyloidogenic peptides, such as $A\beta_{1-42}$ and $A\beta_{25-35}$.

Amyloid peptide-induced MTT formazan exocytosis was determined with B12 cells, as described herein. B12 cells on 35 mm dishes were treated with 10 µM for 16 hr at 37° C., followed by 30 min MTT reduction. The percentage of cells exocytosing MTT formazan with morphology similar to that induced by Aβ was then determined.

TABLE 3

The correlation among amyloid peptides-induced MTT formazan exocytosis, neurotoxicity and glial activation

| Peptide | MTT (%) | Viable Neurons (% of control) | IL-1β (pg/ml) | TNF-α (pg/ml) | Congo red | Fibrils |
|---|---|---|---|---|---|---|
| Control | 0 | 100 | 33 ± 6 | 38 ± 7 | | |
| $A\beta_{25-35}$ | 95 ± 3* | 36 ± 5* | 754 ± 78* | 350 ± 46* | + | + |
| $A\beta_{1-40}$/QQL445 | 93 ± 4* | 47 ± 8* | 537 ± 46* | 274 ± 39* | + | + |
| $A\beta_{1-40}$/WM226 | 0 | 99 ± 3 | 35 ± 9 | 47 ± 11 | − | − |
| $A\beta_{1-40}$/WL508 | 92 ± 3* | 45 ± 5* | 564 ± 63* | 250 ± 43* | + | + |
| $A\beta_{1-40}$/ZM269 | 2 ± 1 | 98 ± 4 | 48 ± 10 | 53 ± 9 | − | − |
| $A\beta_{1-42}$ | 92 ± 4* | 53 ± 8* | 516 ± 65* | 310 ± 58* | + | + |
| Human amylin | 97 ± 1* | 32 ± 7* | 485 ± 58* | 245 ± 56* | + | + |
| Rat amylin | 0 | 101 ± 6 | 46 ± 7 | 48 ± 8 | − | − |

All data are mean ±S.E.M. of three experiments. *: significantly different from control (p<0.05) by two-tailed Student's t-test.

Table 3 shows that peptide preparations that are active in inducing MTT formazan exocytosis are without exception also active in killing hippocampal neurons and increasing glial cytokine production, another indicator of glial activation.

While the invention has been described in detail with reference to certain preferred embodiments thereof, it will be understood that modifications and variations are within the spirit and scope of that which is described and claimed.

What is claimed is:

1. A method of blocking amyloid toxicity in cells, said method comprising contacting said cells with an effective amount of at least one phenyl benzopyranone compound having Structure II, as follows:

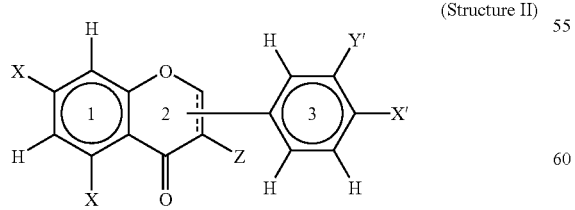

(Structure II)

or enantiomers, diastereomeric isomers or mixtures of any two or more thereof, or pharmaceutically acceptable salts thereof, wherein:
each X is independently OH, SH or $NH_2$;
X' is H, SH, $NH_2$ or OR, wherein R is H or lower alkyl, alkenyl, or alkynyl;
Y' is H, OH, SH, or $NH_2$; and
Z is H, OH, SH or $NH_2$;
provided, however, that at least one of Z and Y' is H, or Z is absent when ring 3 is attached at the 3-position of ring 2.

2. The method of claim 1, wherein said amyloid toxicity is selected from the group consisting of amyloid beta peptide toxicity, amyloid prion protein toxicity, human amylin toxicity, amyloid A protein toxicity, transthyretin toxicity, and AL amyloid toxicity.

3. A method of decreasing amyloid protein production in cells, said method comprising contacting said cells with an effective amount of least one phenyl benzopyranone compound having Structure II, as follows:

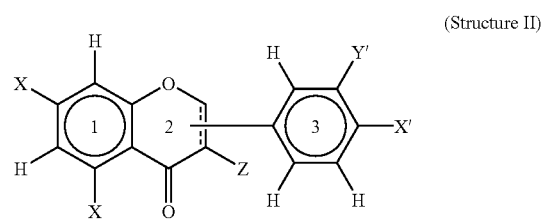

(Structure II)

or enantiomers, diastereomeric isomers or mixtures of any two or more thereof, or pharmaceutically acceptable salts thereof, wherein:
each X is independently OH, SH or $NH_2$;
X' is H, SH, $NH_2$ or OR, wherein R is H or lower alkyl, alkenyl, or alkynyl;
Y' is H, OH, SH, or $NH_2$; and
Z is H, OH, SH or $NH_2$;
provided, however, that at least one of Z and Y' is H, or Z is absent when ring 3 is attached at the 3-position of ring 2.

4. The method of claim 3, wherein said amyloid protein is amyloid beta peptide, amyloid prion protein, islet amyloid protein, or amyloid A protein.

5. A method of inhibiting nerve cell death, said method comprising contacting said nerve cell with an effective amount of least one phenyl benzopyranone compound having Structure II, as follows:

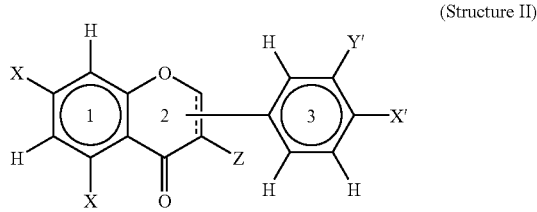
(Structure II)

or enantiomers, diastereomeric isomers or mixtures of any two or more thereof, or pharmaceutically acceptable salts thereof, wherein:
each X is independently OH, SH or $NH_2$;
X' is H, SH, $NH_2$ or OR, wherein R is H or lower alkyl, alkenyl, or alkynyl;
Y' is H, OH, SH, or $NH_2$; and
Z is H, OH, SH or $NH_2$;
provided, however, that at least one of Z and Y' is H, or Z is absent when ring 3 is attached at the 3-position of ring 2.

6. A method of increasing cell viability, said method comprising contacting said cell with an effective amount of at least one phenyl benzopyranone compound having Structure II, as follows:

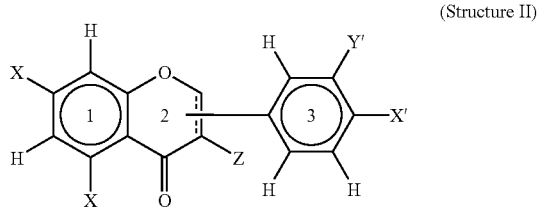
(Structure II)

or enantiomers, diastereomeric isomers or mixtures of any two or more thereof, or pharmaceutically acceptable salts thereof, wherein:
each X is independently OH, SH or $NH_2$;
X' is H, SH, $NH_2$ or OR, wherein R is H or lower alkyl, alkenyl, or alkynyl;
Y' is H, OH, SH, or $NH_2$; and
Z is H, OH, SH or $NH_2$;
provided, however, that at least one of Z and Y' is H, or Z is absent when ring 3 is attached at the 3-position of ring 2.

7. The method according to claim 6, wherein said cell is a nerve cell, a glial cell, a pancreatic cell, an islets of Langerhans cell, an endothelial cell, or an endocrine cell.

8. A method of reducing amyloid deposits in a subject at risk thereof, said method comprising administering to said subject an effective amount of at least one phenyl benzopyranone compound having Structure II, as follows:

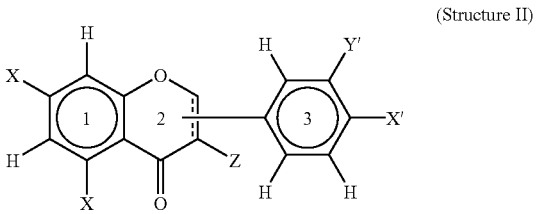
(Structure II)

or enantiomers, diastereomeric isomers or mixtures of any two or more thereof, or pharmaceutically acceptable salts thereof, wherein:
each X is independently OH, SH or $NH_2$;
X' is H, SH, $NH_2$ or OR, wherein R is H or lower alkyl, alkenyl, or alkynyl;
Y' is H, OH, SH, or $NH_2$; and
Z is H, OH, SH or $NH_2$;
provided, however, that at least one of Z and Y' is H, or Z is absent when ring 3 is attached at the 3-position of ring 2.

9. The method according to claim 8, wherein said amyloid deposits are deposits of one or more of amyloid beta peptide, prion protein, islet amyloid protein, amyloid A protein, transthyretin, or AL amyloid.

* * * * *